(12) United States Patent
Guerry (10) Patent No.: US 11,318,075 B2
(45) Date of Patent: May 3, 2022

(54) CONTROLLED RELEASE POLYMER ENCAPSULATED FRAGRANCES

(71) Applicant: RDJE Technologies LLC, Elberon, NJ (US)

(72) Inventor: Raymond E. Guerry, Brick, NJ (US)

(73) Assignee: RDJE TECHNOLOGES LLC, Elberon, NJ (US)

( * ) Notice: Subject to any disclaimer, the term of this patent is extended or adjusted under 35 U.S.C. 154(b) by 0 days.

(21) Appl. No.: 16/039,914

(22) Filed: Jul. 19, 2018

(65) Prior Publication Data

US 2019/0021962 A1    Jan. 24, 2019

Related U.S. Application Data

(60) Provisional application No. 62/534,809, filed on Jul. 20, 2017.

(51) Int. Cl.
| | |
|---|---|
| *A61K 8/11* | (2006.01) |
| *A61K 8/37* | (2006.01) |
| *A61K 8/81* | (2006.01) |
| *A61Q 13/00* | (2006.01) |
| *C11D 3/50* | (2006.01) |
| *B01J 13/16* | (2006.01) |
| *B01J 13/14* | (2006.01) |

(52) U.S. Cl.
CPC .......... *A61K 8/11* (2013.01); *A61K 8/37* (2013.01); *A61K 8/8141* (2013.01); *A61Q 13/00* (2013.01); *B01J 13/16* (2013.01); *C11D 3/505* (2013.01); *A61K 2800/412* (2013.01); *A61K 2800/413* (2013.01); *A61K 2800/56* (2013.01); *B01J 13/14* (2013.01)

(58) Field of Classification Search
CPC ....................................... A61K 8/11
USPC ............................................... 512/4
See application file for complete search history.

(56) References Cited

U.S. PATENT DOCUMENTS

| | | | |
|---|---|---|---|
| 2,800,457 | A | 7/1957 | Green et al. |
| 3,041,288 | A | 6/1962 | Anthony |
| 3,415,758 | A | 12/1968 | Powell et al. |
| 3,516,941 | A | 6/1970 | Matson |
| 3,870,542 | A | 3/1975 | Ida et al. |
| 5,051,305 | A | 9/1991 | Whitaker, Sr. |

(Continued)

FOREIGN PATENT DOCUMENTS

| | | |
|---|---|---|
| EP | 1407753 A1 | 4/2004 |
| EP | 1935483 A2 | 6/2008 |
| EP | 2106704 B1 | 12/2013 |

(Continued)

OTHER PUBLICATIONS

International Search Report issued in PCT/US2018/042869, dated Feb. 8, 2019.
Written Opinion of the International Searching Authority issued in PCT/US2018/042869, dated Feb. 8, 2019.

(Continued)

*Primary Examiner* — Arrie L Reuther
(74) *Attorney, Agent, or Firm* — Fox Rothschild, LLP (57) ABSTRACT

The present disclosure relates to fragrance materials encapsulated within polymeric materials in the form of microcapsules of polymer encapsulated fragrance. The microcapsules are mixed with a water-based binding agent so that a coating forms on the microcapsule in situ, after which the coated microcapsules may be applied to hard surfaces of a product, from which controlled release of the fragrance is provided over time as the product is subjected to normal handling by a user.

17 Claims, 4 Drawing Sheets

(56) References Cited

U.S. PATENT DOCUMENTS

| | | | |
|---|---|---|---|
| 5,112,688 A | 5/1992 | Michael | |
| 6,261,483 B1 | 7/2001 | Frank et al. | |
| 6,329,057 B1 | 12/2001 | Dungworth et al. | |
| 6,869,923 B1 * | 3/2005 | Cunningham | A61K 8/11 510/101 |
| 7,122,512 B2 | 10/2006 | Brain et al. | |
| 8,980,292 B2 | 3/2015 | Dihora et al. | |
| 9,023,783 B2 | 5/2015 | Smets et al. | |
| 2006/0258768 A1 | 11/2006 | Uchiyama et al. | |
| 2009/0209661 A1 | 8/2009 | Somerville Roberts et al. | |
| 2010/0008870 A1 * | 1/2010 | Dihora | A61K 8/11 424/59 |
| 2012/0076864 A1 | 3/2012 | Vandendaele et al. | |

FOREIGN PATENT DOCUMENTS

| | | |
|---|---|---|
| KR | 10-1081960 B1 | 11/2011 |
| WO | 2011056904 A1 | 5/2011 |
| WO | 2016049456 A1 | 3/2016 |
| WO | 2016-144798 A1 | 9/2016 |
| WO | 2016177607 A1 | 11/2016 |

OTHER PUBLICATIONS

Anonymous: "Unconventional Ways to Apply Perfume—Aromi", Jan. 23, 2014 (Jan. 23, 2014), Retrieved from the Internet: URL:<http://www.aromibeauty.com/blog/unconv> entional-ways-to-apply-perfume/.

Extended European Search Report dated May 10, 2021 in EP 18835823.8, 13 pp.

* cited by examiner

CONTROLLED RELEASE POLYMER ENCAPSULATED FRAGRANCES

This application claims the benefit of priority to U.S. Provisional Patent Application No. 62/534,809 filed Jul. 20, 2017, which is hereby incorporated by reference in its entirety.

FIELD

The present disclosure relates to fragrance materials encapsulated within polymeric materials, yielding polymer encapsulated fragrances that may be mixed with a water-based binding agent so that a coating forms on the microcapsule, after which the coated microcapsules may be applied to a hard surface. The present disclosure also relates to products having hard surfaces to which such coated polymer encapsulated fragrances are applied, and from which controlled release of fragrance is achieved over time as the product is subjected to normal use, such as by a consumer.

BACKGROUND

Fragrances are used in numerous products to enhance consumer enjoyment of the product. For example, fragrances can be added to personal care products such as soaps, shampoos, body washes, and deodorants. To enhance the effectiveness of a fragrance for the user, various technologies have been employed to deliver the fragrance at the desired time. One such technology involves encapsulation of a fragrance material in a protective coating, such as a polymeric material, which protects the fragrance from evaporating, reacting, oxidizing or otherwise dissipating until needed. Examples of known encapsulates and encapsulated fragrances are described in U.S. Pat. Nos. 2,800,457, 3,870,542, 3,516,941, 3,415,758, 3,041,288, 5,112,688, 6,329,057, 6,261,483, 7,122,512, 9,023,783, and the Kirk-Othmer Encyclopedia of Chemical Technology.

While encapsulating a fragrance material within a polymeric microcapsule can help prevent fragrance degradation and loss, conventional encapsulated fragrances are not sufficient to provide fragrance performance on an as-needed basis over a long period of time. Thus, it would be beneficial to provide polymer encapsulated fragrances that can be added to consumer products and provide controlled release of fragrance materials over time, and wherein the fragrance can continue to be released in response to repeated normal use of the product by a consumer over time.

SUMMARY

The present disclosure relates generally to fragrance materials encapsulated within polymeric materials in the form of microcapsules of polymer encapsulated fragrance. The microcapsules are coated with a water-based binding agent and may then be applied to a hard surface of a product, from which controlled release of the fragrance is provided over time as the product is subjected to normal handling by a user.

In one aspect, the disclosed technology relates to a treatment solution for application to a hard surface, including water; and a composition including a fragrance material encapsulated within polymeric materials in the form of microcapsules of polymer encapsulated fragrance, wherein the water solubility of the fragrance material is 0.001 mol/L or less, and a binding agent having a water solubility of at least 0.1 mol/L, wherein the binding agent covers at least 80% of an outer surface of the microcapsules; wherein the treatment solution contains water as the only solvent outside of the microcapsules, and wherein the microcapsules do not contain any surfactants or fixatives. In one embodiment, a weight ratio of binding agent to microcapsule is in the range of about 1:1 to about 4:1. In another embodiment, the binding agent is a cross-linked acrylate polymer. In another embodiment, the treatment solution includes 10 vol % microcapsules and 10 vol % binding agent. In another embodiment, the fragrance material is in the form of a liquid. In another embodiment, the fragrance material includes an aroma selected from food, vegetable, fruit, plant, floral, spice, and natural environment aromas, and combinations thereof, dispersed in a non-aqueous liquid. In another embodiment, the fragrance material includes isopropyl myristate, diethyl phthalate, or a combination thereof. In another embodiment, the microcapsules include fragrance material in an amount of about 0.1% to about 50% by weight, based on the total weight of the microcapsules. In another embodiment, the microcapsules have an average diameter of about 0.01 µm to about 300 µm. In another embodiment, the microcapsules include an outer polymeric shell and an inner liquid core, wherein a weight ratio of shell to core is 1:10 to 1:500. In another embodiment, the binding agent includes reactive functional groups capable of chemically binding to a hard surface, wherein the reactive functional groups include one or more groups selected from acid anhydride groups, amino groups, N-substituted amino groups, epoxy groups, glycidyl groups, hydroxyl groups, isocyanate groups, urea groups, aldehyde groups, ester groups, ether groups, alkenyl groups, alkynyl groups, thiol groups, disulphide groups, silyl groups, silane groups, glyoxal-based groups, aziridine-based groups, 2,4-pentadione, malonic acid, acetylacetone, ethyl acetone acetate, malonamide, acetoacetamide and its methyl analogues, ethyl acetoacetate, isopropyl acetoacetate, halo groups, hydrides, and combinations thereof.

In another aspect, the disclosed technology relates to a method of applying an encapsulated fragrance to a hard surface, including applying the treatment solution to a hard surface of a product; and drying the hard surface. In one embodiment, the hard surface is at least a portion of a hair application tool. In another embodiment, the drying includes evaporation. In another embodiment, the drying step results in the formation of a transparent film.

In another aspect, the disclosed technology relates to a method of applying fragrance to hair, including obtaining a hair application tool having a hard surface treated with the treatment solution; and manipulating a subject's hair with the hair application tool. In one embodiment, the hair application tool includes a hairbrush, comb, hair accessory, or combination thereof.

In another aspect, the disclosed technology relates to a hair application tool for controlled release of fragrance to a subject's hair, including a hair application tool having a hard surface treated with a treatment solution including water and a composition including: a fragrance material encapsulated within polymeric materials in the form of microcapsules of polymer encapsulated fragrance, wherein the water solubility of the fragrance material is 0.001 mol/L or less, and a binding agent having a water solubility of at least 0.1 mol/L, wherein the binding agent covers at least 80% of an outer surface of the microcapsules; wherein the treatment solution contains water as the only solvent outside of the microcapsules, wherein the microcapsules do not contain any surfactants or fixatives, and wherein the hair application tool has a rupture profile whereby only 10-50% of the microcapsules rupture after 100 hair application strokes. In one embodiment, the hair application tool includes a hairbrush, comb, hair accessory, or combination thereof. In another embodiment, the treated hard surface includes a transparent film including the microcapsules.

BRIEF DESCRIPTION OF THE DRAWINGS

The accompanying drawings, which are incorporated herein and constitute part of this specification, illustrate non-limiting and non-exhaustive embodiments of the present disclosure, and, together with the description provided herein, serve to explain various features of the invention.

DETAILED DESCRIPTION

The present disclosure describes compositions containing fragrance materials encapsulated within polymeric materials wherein the polymer encapsulated fragrance is coated with a water-based binding agent. The present disclosure further describes products having hard surfaces to which the compositions are applied, wherein controlled release of the fragrance is achieved in response to repeated use of the product.

Fragrance Materials

Fragrance materials that are suitable for use in this invention are not generally limited and include, for example, essential oils, fixed oils, plant extracts, resins or resinoids, fragrance chemicals, floral water, and combinations thereof. Essential oils refer to any volatile aromatic liquid essence that is extracted by steam, distillation, expression, solvent extraction or other means from aromatic plants such as flowers, grasses, fruits, leaves, roots, and/or trees. Fragrance chemicals may include, but are not limited to: synthetic odoriferous chemicals, including complex compositions obtained using two or more odoriferous products as a mixture; excipient products that ensure homogeneity of the fragrance chemical; aliphatic or aromatic ketones; aliphatic or aromatic aldehydes; condensation products of aldehydes and amines; aliphatic or aromatic alcohols; aliphatic or aromatic lactones; aliphatic or aromatic ethers or esters; linear, cyclic, or aromatic saturated or unsaturated hydrocarbons; terpenes, which may or may not be polynuclear; and any combinations thereof. Preferably, the fragrance material is in the form of a liquid.

In general, suitable fragrance materials can be released to the environment to create a pleasant aroma. Examples of aromas that can be produced by suitable fragrance materials for use herewith include, but are not limited to, food, vegetable, fruit, plant, floral, spice, and natural environment aromas—e.g., acacia, almond, anise, apple, apricot, baby powder, baked apple, balsam, bamboo, banana, banana flower, berry, black cherry, blueberry, bread, butter, cake, camphor, cantaloupe, caramel, caraway, carnation, cassie, cedar, cedar wood vanilla, cheese, cherry, chocolate, chypre, cinnamon, citronella, citrus, clover, coffee, coconut, cookie, cotton, cotton candy, cream, cucumber, cyclamen, earth, evergreen, fern, freesia, freshly-cut hay, gardenia, garlic, geranium, golden apple, grape, grapefruit, green tea, hawthorn, hazelnut, heliotrope, herbs, hibiscus, honey, honeydew, honeysuckle, hyacinth, iris, jam, jasmine, jonquil, lavender, lemon, lemongrass, lilac, lily, lime, magnolia, mandarin cassis, mango, marigold, melon, mimosa, mint, moss, mulberry, musk, narcissus, nectarine, nut, onion, orange, orange blossom, orchid, peach, peanut, pear, pepper, peppermint, pine, pineapple, pistachio, pizza, plum, pomegranate, popcorn, potpourri, pumpkin, quince, rainwater, raspberry, reseda, rose, rosemary, Russian olive, sage, sandalwood, sea water, smoke, spearmint, spruce, strawberry, sweet pea, thyme, trefle, tropical, tuberose, vanilla, violet, wallflower, walnut, watermelon, wine, wood, and any combinations thereof.

The fragrance material is "insoluble" in water, which means that it has a solubility of 0.001 mol/L or less. The fragrance material must not be highly water soluble, water soluble, or even slightly water soluble. Accordingly, glycols such as dipropylene glycol, light alcohols, and highly water soluble fragrance alcohols should not be included in the compositions disclosed herein. In one embodiment, the fragrance material includes isopropyl myristate, diethyl phthalate, or both.

In some embodiments, the fragrance materials include highly hydrophobic materials that tend to remain in a dispersed phase and partition only slightly into aqueous solution. In some embodiments, the fragrance material has a c Log P value of 2 or more, such as 3 or more, or 5 or more, so as to produce microcapsules that contain cores most similar to the original composition, and are thus less likely to react with materials that form the microcapsule shell. Fragrance materials having a c Log P value below 2 are likely to remain in the water phase and/or cause the encapsulation to fail.

In at least one embodiment, the fragrance material is dispersed in a non-aqueous liquid (containing, for example, polymers, pre-condensates, or the like) prior to being encapsulated within the polymeric microcapsule walls. In one embodiment, the amount of water in the non-aqueous liquid is less than 0.1% by weight. In another embodiment, the non-aqueous liquid is a water-immiscible liquid. This assists in the formation of the microcapsules by an emulsion polymerization route. Non-limiting examples of suitable water-immiscible liquids include organic oils, silicone oils, fluorocarbons, and mixtures thereof.

The fragrance material should be highly concentrated to provide maximum effect, and the use of diluents should be minimized. Thus, the fragrance material may be 100% concentrated or may be diluted with an organic diluent to a concentration of at least 75% by weight, such as 80% by weight, 90% by weight, 95% by weight, or 99% by weight. Preferably, the organic diluent is a monoester, such as a monoester of a fatty alcohol or fatty acid. In one embodiment, the organic diluent is isopropyl myristate, benzyl benzoate. Light phthalates are not suitable diluents.

In one embodiment, the amount of fragrance material in the microcapsule is about 0.1% to about 50% by weight, such as about 10% to about 30% by weight, based on the total weight of the microcapsule (uncoated).

The amount of fragrance material in the compositions disclosed herein varies from about 5 wt % to about 95 wt %, such as from about 40 wt % to about 90 wt %, or from about 50 wt % to about 80 wt %, on a dry basis. The fragrance material may also be combined with other materials, such as one or more solvents (having a water solubility of 0.001 mol/L or less) that serve to increase the compatibility of the various materials, increase the overall hydrophobicity of the blend, influence the vapor pressure of the materials, or help structure the blend. Solvents that can perform one or more of these functions include, for example, mineral oils, triglyceride oils, silicone oils, fats, waxes, fatty alcohols, diisodecyl adipate, and diethyl phthalate. Other materials that may be combined with the encapsulated fragrance materials include, for example, sunscreens, softening agents, insect repellents, hair treatments (shampoos, conditioners, etc.), and the like.

Polymeric Materials/Microcapsule Shell

The microcapsules disclosed herein can provide delivery of a fragrance material onto a hard surface by rupture, and in such case the microcapsules are suitably of a friable nature—i.e., arranged for rupture during use, subsequent to application onto a surface. This may be arranged by choice of the strength of material making up the shell of the microcapsule and its wall thickness. In general, the microcapsule has a shell having an outer face and an inner face, the inner face forming an enclosure for encapsulating the fragrance material.

Microcapsules useful in the present invention may have a liquid core containing the fragrance material, and a thin polymeric shell completely surrounding the liquid core. By encapsulating the fragrance material in liquid in a shell, the fragrance material is protected throughout the process of application of the microcapsule to a surface. Typically, the shell is of a water-insoluble material—i.e., having a water solubility of 0.001 mol/L or less.

The shell material can be any suitable polymeric material that is impervious to the materials in the liquid core and also impervious to the materials which may come in contact with the outer surface of the shell. The microcapsule shell wall can be composed of a wide variety of polymeric materials including gelatin, polyurethane, polyolefin, polyamide, polyester, polyolefin, protein, polysaccharide, modified cellulose, gums, polyacrylate, polystyrene, polyesters, lipids, silicone and siloxane resins, chitosan, epoxy resins, and combinations thereof. In one embodiment, the materials for the microcapsule shell wall are aminoplast polymers including the reactive products of, for instance, urea or melamine and aldehyde (e.g., formaldehyde). Such materials include those which are capable of acid condition polymerization from a water-soluble prepolymer or precondensate state. Polymers formed from such precondensate materials under acid conditions are water-insoluble and can provide the requisite friability characteristics to allow subsequent rupture of the microcapsule.

Examples of suitable polysaccharides include, but are not limited to, guar, alginates, starch, xanthan, chitosan, cellulose, dextrans, arabic gum, carrageenan, hyaluronates, and combinations thereof.

Examples of suitable polyacrylates include compounds with up to five different types of monomers, each monomer having the generic formula —CH($R_1$)—C($R_2$)—(CO—$R_3$—$R_4$)—. In this formula, $R_1$ is selected from H, $C_{1-25}$ aliphatic moieties (alkane or alkene) with 0-5 double bonds, aromatic moieties, polysiloxane, and $C_{1-25}$ alkoxylated fatty alcohol; $R_2$ is selected from H and $CH_3$; $R_3$ is selected from $C_{1-25}$ alkyl alcohol and alkylene oxide, or $R_3$ may be absent; and $R_4$ is selected from —$NH_2$, —$NHR_1$, —$NR_1R_2$, —$NR_1R_2R_5$ (where $R_5$ is selected from $R_1$, $R_2$, and —$CH_2$—COOH), —NH—C(O)—, sulfo betaine, betaine, polyethylene oxide, poly(ethyleneoxide/propylene oxide/butylene oxide) grafts, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —COOH alkali salt, sulfonate, ethoxy sulphate, pyrrolidone, caprolactam, phenyl-$R_6$, and naphthalene-$R_6$ (where $R_6$ is selected from $R_1$, $R_2$, $R_3$, sulfonic acid, and mixtures thereof).

In at least one embodiment, the microcapsule shell is a cross-linked polymer, such as cross-linked melamine formaldehyde, cross-linked urea formaldehyde, or a mixture thereof.

Microcapsules as described above can be prepared by known processes for producing capsules of the requisite size, friability and water-insolubility. Generally, methods such as coacervation (e.g., simple or complex coacervation of gelatin) and interfacial polymerization can be employed in a known manner to produce suitable microcapsules.

Microcapsules made from aminoplast polymer shell materials can be made by an interfacial polymerization process. For example, an aqueous solution of a precondensate (methylol urea) is formed containing about 3% to about 30% by weight of the precondensate. In one embodiment, a water-insoluble liquid core material, such as a hydrophobic oil, is dispersed throughout this solution in the form of microscopically-sized discrete droplets. While maintaining solution temperature of 20° C. to 90° C., acid is added to catalyze polymerization of the dissolved precondensate. If the solution is rapidly agitated during this polymerization step, shells of water-insoluble aminoplast polymer form around and encapsulate the dispersed droplets of liquid core material. Capsules suitable for use in the present invention may be produced by a similar method, with the fragrance material dispersed through the hydrophobic liquid core material prior to polymerization. In one embodiment, the polymer of the shell is a melamine formaldehyde resin or includes a layer of this polymer.

Typically, the microcapsules vary in size, and may have average diameters of about 0.01 to about 300 μm, such as about 0.05 to about 100 μm, or about 2 to about 50 μm. The proportion by weight of shell with respect to the liquid core will typically be from 1:10 to 1:500, such as 1:20 to 1:100. If the proportion is lower than 1:500 the resultant shell may be too thin, allowing excess microcapsules to rupture prematurely. If the proportion is higher than 1:10, the resultant wall may be too strong to rupture as needed. The exact details will depend upon the shell used.

In one embodiment, at least 75%, 85% or even 90% of the microcapsules have a shell wall thickness of about 30 nm to about 250 nm, such as about 40 nm to about 180 nm, or about 50 nm to about 150 nm.

As noted above, the microcapsules of the present invention must be friable in nature. Friability refers to the propensity of the microcapsules to rupture or break open when subjected to direct external pressures or shear forces. For purposes of the present invention, the microcapsules are "friable" if, while attached to hard surfaces, they may be ruptured in order to release the liquid core. For instance, if the hard surface is a plastic hairbrush, comb or hair accessory, the microcapsules should rupture as a result of shear forces caused by normal handling or use during hair care—e.g., brushing, combing, manipulation of accessories, etc.

In one embodiment, at least a portion (e.g., all or substantially all) of the outer face of the shell of the microcapsule is coated with a binding agent, wherein the binding agent coating includes suitable reactive functional groups such that the coating is chemically bondable to the hard surface. This enables the microcapsules to bond or be bonded to suitable surfaces without the need for a separate adhesive composition being applied to the surface itself. Such adhesive compositions may alter the feel or texture of the surface of a product and thus may be undesirable. Preferably, the reactive functional group includes a reactive moiety adapted to provide covalent bonding to the hard surface.

Non-limiting examples of suitable reactive functional groups include groups such as acid anhydride groups, amino groups, N-substituted amino groups and their salts, epoxy groups (such as cyclohexyl epoxy groups), glycidyl groups, hydroxyl groups, isocyanate groups, urea groups, aldehyde groups, ester groups, ether groups, alkenyl groups, alkynyl groups, thiol groups, disulphide groups, silyl or silane groups, glyoxal-based groups, aziridine-based groups, groups based on active methylene compounds or other b-dicarbonyl compounds (such as 2,4-pentadione, malonic acid, acetylacetone, ethylacetone acetate, malonamide, acetoacetamide and its methyl analogues, ethyl acetoacetate and isopropyl acetoacetate), halo groups and hydrides. Polar groups (i.e. positively or negatively charged, zwitterionic or amphoteric groups) or hydrogen bonding groups may also be considered as reactive functional groups, but groups having reactive moieties providing covalent bonding are preferred.

The chemical bonds can be ionic, hydrogen bonding or, better still, covalent, where a simple chemical reaction takes place by addition or substitution. Reaction may be promoted solely by the pH of the solution in which the coated microcapsules are applied to the surface, normally an alkaline solution, or initiators may be included in case of an addition radical reaction. Covalent bonds are more resistant and ensure the permanence of bonding of the microcapsules to the hard surface.

For surfaces with cationic charges, negative charges may be introduced into the binding agent coating, for instance by means of functional groups with negative charges, which will impart affinity between coated microcapsules and hard surfaces, providing a strong bond between the two. Other groups, such as epoxy groups, may be incorporated into the coating by suitable copolymerization.

For aminoplast resins such as urea- or melamine-formaldehyde, co-monomers containing functional groups may be introduced. For instance, glycidyl methacrylate or any other suitable monomer that may contain epoxy (glycidyl) groups, or acrylic acid containing carboxylic groups may be used.

In one embodiment, the microcapsule may have an outer shell of melamine-formaldehyde coated with a vinyl polymer as the binding agent, wherein the monomer used for forming the vinyl polymer contains a functional group that will form ionic bonds with a hard surface, or functional groups that may react with the hard surface to form covalent bonds.

Where the outer face is of an aminoplast resin such as urea-formaldehyde or melamine-formaldehyde, or is a polyamide or chitosan, the introduction of functional groups, such as epoxy groups or ethyl chlorine, for example, may be achieved through a reaction between unreacted free amine groups and a bifunctional bridging agent (i.e., bonding agent) that contains epoxy groups, alkyl groups substituted with a halogens vinyl groups or heterocyclic, leaving the other group of the bifunctional agent free for reacting with the surface.

Functional reactive groups of the binding agent coating are preferably adapted to react with a second functional group of a hard surface, whereby a covalent bond is formed between the functional reactive group of the microcapsule and the second functional group of the surface. The reactive moiety may be adapted to provide covalent bonding to the surface.

The polymer encapsulated fragrances disclosed herein may be prepared by microencapsulation techniques known to those of skill in the art. Appropriate microencapsulation processes include both physical and chemical techniques, as described in further detail below.

Polymer Encapsulation of Fragrance Material

In general, the term encapsulated is intended to mean that the fragrance material is substantially covered in its entirety. Encapsulation can provide pore vacancies or interstitial openings depending on the encapsulation techniques employed. In at least one embodiment, the entire portion of the fragrance material is encapsulated.

In one embodiment, microcapsules are prepared through the following process. A non-aqueous solvent solution containing a water-insoluble polymerizing compound such as a prepolymer, a polymerizable monomer, an existing polymer, or combinations thereof is combined with a desired water-insoluble fragrance material and dispersed in an aqueous solution containing dispersing agent or protective colloid and hardening agent for the polymerizing compound or in water, resulting in a dispersion or slurry of microcapsules of encapsulated fragrance materials. Generally, the dispersing is carried out by slowly dropping the water-insoluble components (simultaneously, or one after the other in either order) into the aqueous solution or water while vigorously stirring (e.g., using a high shear mixer). In this dispersion, the polymerizing compound is interfacially polymerized at the interfaces between the dispersed water-insoluble particles and the aqueous solution or water. The interfacially polymerized polymer forms the wall constituent of the microcapsules. The wall constituent contains the water-insoluble fragrance materials that form the core, and are preferably the main component of the core.

In one embodiment, the formation of microcapsule walls encapsulating the fragrance is enhanced by adjusting the mixture of polymeric and fragrance materials to a pH in the range of 3 to 8.5 and heating the mixture to 50-85° C.

A representative process for aminoplast encapsulation is disclosed in U.S. Pat. No. 3,516,941; and a representative process for gelatin encapsulation is disclosed in U.S. Pat. No. 2,800,457, but many variations of materials and process steps for each such process are also possible. See also U.S. Pat. Nos. 4,145,184 and 5,112,688.

In one embodiment, the weight ratio of the encapsulating polymer to the fragrance material is from about 1:1 to about 1:25, such as from about 1:10 to about 1:20. For example, if an encapsulated fragrance contains 20 wt % fragrance material and 20 wt % encapsulating polymer, the weight ratio would be 1:1.

In one embodiment, at least 75% (e.g., 85% or 90%) of the microcapsules have a fracture strength of 0.1-5.0 MPa, such as 0.2-3.0 MPa, 0.2-2.0 MPa, or 0.2-1.2 MPa.

In general, the use of highly lipophilic ingredients can make it easier to manufacture the polymer encapsulated fragrances.

In at least one embodiment, the microcapsule is formed without the addition of surfactants (e.g., alkyl ethoxylate, alkyl ethoxylated sulfates, ethoxylated carboxylate sulfates, nonyl phenol ethoxylate, tween, and other non-ionic and anionic surfactants). In at least one embodiment, the microcapsule is formed without the addition of fixatives (e.g., extracts of labdanum or styrax, abietic acid derivatives and the like), such that the microcapsules contain no surfactants or fixatives. Without being bound by any one theory, it is believed that surfactants and fixatives may interfere with proper formation of the capsule wall of the microcapsules disclosed herein.

In at least one embodiment, the microcapsule is formed without the use of electrolytes (catalysts), such that the treatment solution contains no electrolytes. It has been determined that a treatment solution containing electrolytes delivers poor initial performance as compared to a treatment solution containing no electrolytes.

Water-Based Binding Agent Coating

The polymer encapsulated fragrance may be coated with a binding agent (i.e., an adhesive) to assist in adhering the microcapsules to a hard surface. The binding agent is water-based and provided in an aqueous solution containing only water soluble or highly water soluble ingredients (i.e., having a water solubility of at least 0.1 mol/L).

In at least one embodiment, the binding agent is dissolved in water and no other solvent(s). For example, in one embodiment, the binding agent solution does not contain ethanol, isopropanol, polyols such as ethylene glycol, propylene glycol, and glycerol, highly polar organic solvents such as pyrrolidine, acetamide, ethylene diamine, and piperazine, humectants/plasticizers for polar polymers such as monosaccharides (glucose, sucrose), amino acids, ureas and hydroxyethyl modified ureas, plasticizers for less polar polymers such as diisodecyl adipate, phthalate esters, and/or combinations thereof. Without being bound by any one theory, it is believed that the use of non-water solvents in the binding agent solution has a negative impact on stability and can cause the microcapsules to rupture prematurely. Other problems believed to be associated with the use of non-water solvents in the binding agent solution include possible gloss, slip, and haze. Additionally, it has been determined that including a non-water solvent such as a drying aid in the preparation of the treatment solution delivers poor initial performance as compared to a treatment solution prepared without a non-water drying aid solvent.

In one embodiment, the binding agent component amounts to 5-40% w/w of the binding agent solution, such as 10-20% w/w, the remainder being water. In one embodiment, the amount of binding agent is 0.1 to 3 wt %, based on the total weight of the composition.

The binding agent acts as an adhesive to adhere the microcapsules to hard surfaces but still allow the microcapsules to rupture and release fragrance as desired, such as by normal physical use of the hard surface product, resulting in controlled release of the fragrance as needed over an extended period of time. Further, the binding agent adheres microcapsules to a hard surface by entrapment or adhesive forces. As a non-limiting example, an acrylic polymer, polyurethane resin, or combination thereof would serve as a suitable binding agent.

Other suitable binding agents for use herewith include but are not limited to acrylate polymers. For example, the binding agent may be an acrylic acid homopolymer or a copolymer or ester of acrylic acid. In one embodiment, the binding agent is ACRYGEN® 27 (available from Omnova Solutions), a liquid self-crosslinking acrylic binder that is white in color, has a glass transition temperature (Tg) of 30° C., a Brookfield Viscosity of <100 cps, and a density of 8.9 lbs/gal. In another embodiment, the binding agent is ACRYGEN® 61192 (available from Omnova Solutions), a liquid acrylic binder that is white in color, has a glass transition temperature (Tg) of −12° C., and a Brookfield Viscosity of <30 cps.

In at least one embodiment, the binding agent is cross-linked, such as a cross-linked acrylate polymer.

The binding agent coating covers the majority of the microcapsule. In one embodiment, the coating covers at least 80% of the microcapsule, such as 90% and 100% coverage.

In another embodiment, the amount of binding agent is 1-3000%, such as 5-1000%, or 10-500% of the weight of the microcapsule. In another embodiment, the weight ratio of binding agent to microcapsule is in the range of about 1:1 to about 4:1.

In one embodiment, a binding agent is dissolved in water and mixed with a suspension or slurry of coated microcapsules prior to application to the hard surface of a final product. Other modes of coating the microcapsules are also possible, such as drying the coating solution in combination with the capsule suspension, or using higher concentrations of coating such that a gel structure is formed, or combining the coating material with other polymers or adjuvants which serve to improve physical characteristics or base compatibility. Drying or reducing the water content of the capsule suspension prior to coating is also possible.

Coating polymer(s) may also be added to a suspension of microcapsules that contains reactive components such that the coating becomes chemically (e.g., covalently) bonded to the capsule shell, or the coating polymer(s) may be added during crosslinking stage of the capsule shell to allow partial covalent bonding of the coating.

Composition: Coated Polymer Encapsulated Fragrance

In one embodiment, the composition is provided in a homogenous aqueous solution. In another embodiment, the composition has a pH of 3 to 8.5, such as a pH range of 3 to 5. The composition may be colorless, particularly in the pH range of 3 to 8.5 or 3 to 5. Preferably, the composition forms a transparent film when dried.

In one embodiment, the amount of microcapsules present in the composition is about 0.1% to about 50% by weight, such as about 0.2 to about 30% by weight, or about 0.3 to about 20% by weight, depending upon how the composition is to be used.

In general, the average particle size of the composition is about 0.05 μm to about 1000 μm, such as about 1 μm to about 500 μm, about 1 μm to about 100 μm, or about 2 μm to about 15 μm. The particle size distribution can be narrow, broad, or multi-modal. Each mode of a multi-modal distributions may be composed of different types of capsule chemistries. For example, in one embodiment, at least 75%, 85% or 90% of the particles may have a particle size of about 1 μm to about 100 μm, such as about 5 μm to about 80 μm, about 6 μm to about 50 μm, or about 15 μm to about 40 μm.

Application of Treatment Solution to Hard Surfaces

Compositions disclosed herein (i.e., coated polymer encapsulated fragrances) may be dispersed in a treatment solution and applied to any hard surface. Some examples of suitable hard surfaces include, but are not limited to, plastic, glass, ceramic, wood, fiberglass, metal, stone, coated surfaces, painted surfaces, and combinations thereof.

In one embodiment, the treatment solution is an aqueous solution. Preferably, the composition is stably dispersed within the treatment solution. For example, the treatment solution may contain the composition dispersed in water, wherein the water is present in an amount of at least 80% by weight, such as 90% by weight. The use of water enhances the ability of the hard surface to dry by evaporation after being treated with the treatment solution. In one embodiment, after the hard surface is treated with the treatment solution, the binding agent remains along with unruptured microcapsules on the hard surface after the rest of the treatment solution has evaporated. Where the treatment solution is aqueous, a natural or forced evaporative drying process may be used. Typically, the microcapsules of the composition are applied to the hard surface in an amount of 0.1 to 20 g/m$^2$ of surface, such as 0.2 to 10 g/m$^2$, 0.3 to 5 g/m$^2$, or 0.5 to 3 g/m$^2$. At these levels, there are sufficient microcapsules to provide the desired strength and duration of fragrance without the presence of the microcapsules leading to a major change in the appearance or texture of the surface.

Another aspect of the present disclosure relates to a method for treating a hard surface with the treatment solution that includes the steps of preparing a treatment solution by dispersing a composition disclosed herein in an aqueous solution, and then applying the treatment solution to the hard surface, whereby coated polymer encapsulated fragrances are effectively deposited on the hard surface. In at least one embodiment, after the treatment solution deposited on the hard surface is dry, a resulting film is formed on the hard surface, which covers all or substantially all of the hard surface. Preferably, the dried film is transparent.

In general, the compositions can be applied to a hard surface by any suitable process such as padding, spraying or wiping, with the microcapsules dispersed in a liquid as set out herein. Other suitable application techniques include dip coating, brush coating, spray coating, pattern coating such as rotogravure coating, and print coating employing printing technologies such as flexographic printing (e.g., using an anilox roll). In at least one embodiment, heat is applied during the application process.

Release of Fragrance from Polymer Capsules

Another aspect of the present disclosure relates to a method for applying fragrance to a target, such as by transferring to a target fragrance released from coated polymer encapsulated fragrances deposited on a hard surface. For instance, once the compositions disclosed herein are applied to or deposited on a hard surface, it is desirable for fragrance to be released from the capsules by physical or mechanical means, by large-scale rupture of the capsule wall, by diffusion through the capsule wall, or by small cracks or imperfections in the capsule wall caused by drying. In one embodiment, the method may be performed by an end user of a consumer product—e.g., applying fragrance from a hard surfaced hairbrush to hair. In each such instance, the volatility of the encapsulated fragrance material is important to both the speed and duration of release, which in turn impacts consumer perception. Fragrance materials having higher volatility (e.g., boiling point of less than about 250° C., preferably less than about 225° C.) are preferred when quick release and quick impact of fragrance is desired. Conversely, fragrance materials having lower volatility (e.g., boiling point of more than 225° C.) are preferred when a longer duration of aroma is desired. Fragrance materials having varying volatility may also be combined in any proportions in order to achieve the desired speed and duration of release.

In one embodiment, after drying the surface following application of the treatment solution, microcapsules are later mechanically ruptured in order to release fragrance from the surface. In general, such mechanical rupturing of the microcapsules takes place as a result of forces to which the microcapsules are subjected during the normal use of the surface. For instance, if the surface is a hard surface such as a hair application tool (e.g., hairbrush or comb), rupture may take place when a consumer uses the tool on a subject's hair, so that the released fragrance is transferred from the tool to the hair. For instance, the tool could be used to brush hair on the head of a human (male or female), or the hair of other mammals (e.g., dogs, cats, etc.) In this manner, the product provides long lasting fragrance with each use. Typically, larger microcapsules are more easily ruptured whereas smaller microcapsules may need greater forces to lead to rupture. It is desirable to provide polydisperse microcapsules (i.e., microcapsules of various sizes).

To provide a high fragrance impact, fragrance materials having a high odor-activity are preferred. Materials with high odor-activity can be detected by sensory receptors at low concentrations in air, thus providing high fragrance perception from low levels of deposited compositions. Yet, this property must be balanced with volatility, as described above.

In one embodiment, about 0.01 to 1% of the microcapsules rupture per each normal use of the product comprising the hard surface. For example, when the product is a hairbrush, the rupture profile of the hairbrush may be such that only about 10-50% of the microcapsules (preferably, about 10-20%) have ruptured after 100 brush strokes, about 40-80% of the microcapsules (preferably, about 40-50%) have ruptured after 500 brush strokes, and about 90-100% of the microcapsules have ruptured after 1000 brush strokes.

EXAMPLES

The present invention is next described by means of the following examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Example 1

Preparation of Microcapsule

This example is directed to the preparation of a microcapsule having a fragrance material encapsulated within polymeric materials. A copolymer of polyacrylamide and acrylic acid is dispersed in water together with a methylated melamine-formaldehyde resin to form a dispersion of polymeric material. A fragrance material comprising a tropical-scented essential oil is added to the dispersion of polymeric material and mixed under high speed shearing at 60-70° C. for two hours, yielding small droplets of polymer encapsulated fragrance.

Example 2

Addition of Binding Agent Coating to Produce Treatment Solution

This example is directed to the application of a binding agent coating to the outer shell surface of microcapsules having a fragrance material encapsulated within polymeric materials. The polymer encapsulated fragrance of Example 1 is added to water and mixed together with a cross-linked acrylate polymer (ACRYGEN® 27), such that the binding agent solution contains 10 vol % microcapsules and 10 vol % binding agent, yielding an aqueous solution of microcapsules of polymer encapsulated fragrance coated with binding agent. This resulting aqueous solution is an example of a treatment solution for application to hard surfaces.

Example 3

Stability and Durability Testing and Evaluation

This example is directed to stability and durability testing and evaluation of a hairbrush treated with a treatment solution of the present disclosure. Prepare four treatment solutions as in Example 2 but containing one of the following binding agents: (A) ACRYGEN® 27, (B) ACRYGEN® 61192, (C) CARBOPOL® 941, or (D) acrylic floor wax.

Figure 1:
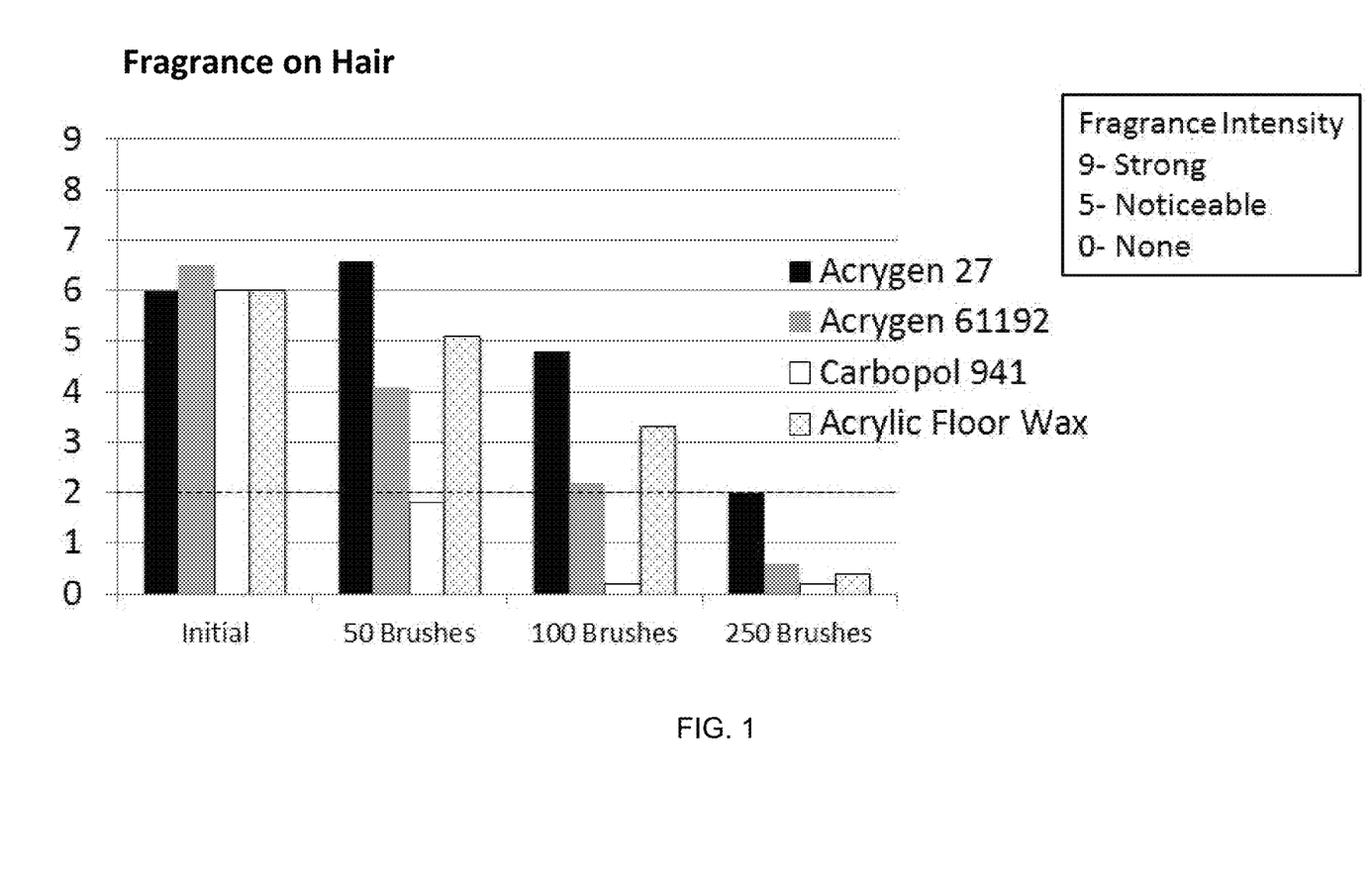
FIG. 1 is a graph showing fragrance intensity over time for a hairbrush as measured from initial use (5 brush strokes) up to 250 brush strokes, wherein the hairbrush has a hard surface to which a composition disclosed herein was applied, as described in Example 3.
Figure 2A:
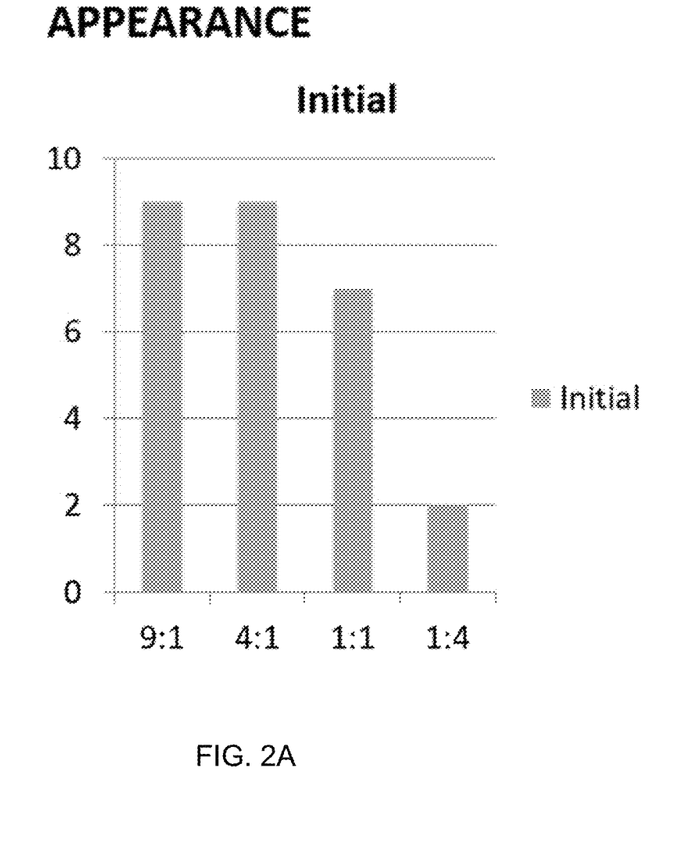
FIG. 2A is a graph related to the initial appearance of hairbrushes treated with treatment solutions having weight ratios of binding agent to microcapsules of 9:1, 4:1, 1:1, and 1:4, respectively.
Figure 2B:
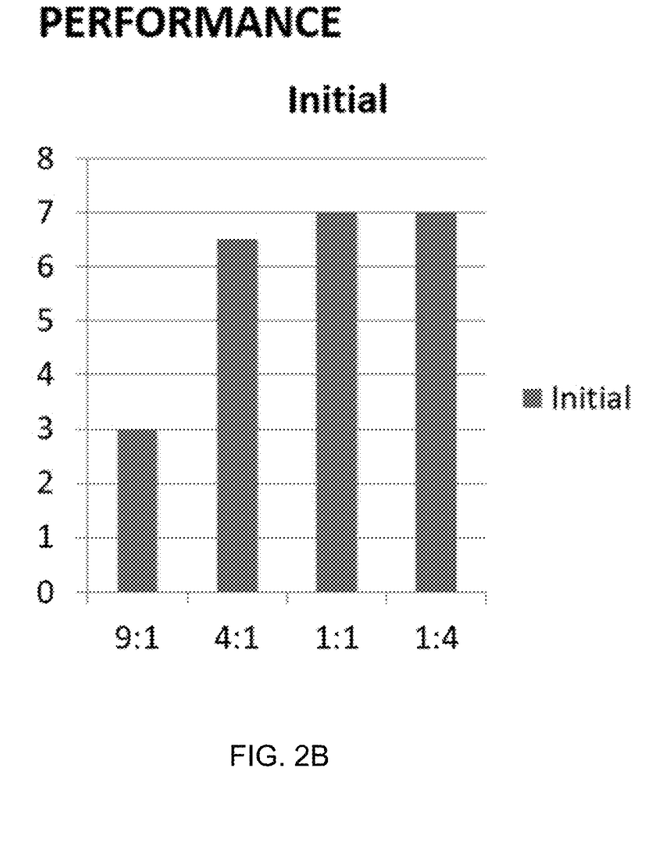
FIG. 2B is a graph related to the initial performance of hairbrushes treated with treatment solutions having weight ratios of binding agent to microcapsules of 9:1, 4:1, 1:1, and 1:4, respectively.
Figure 3:
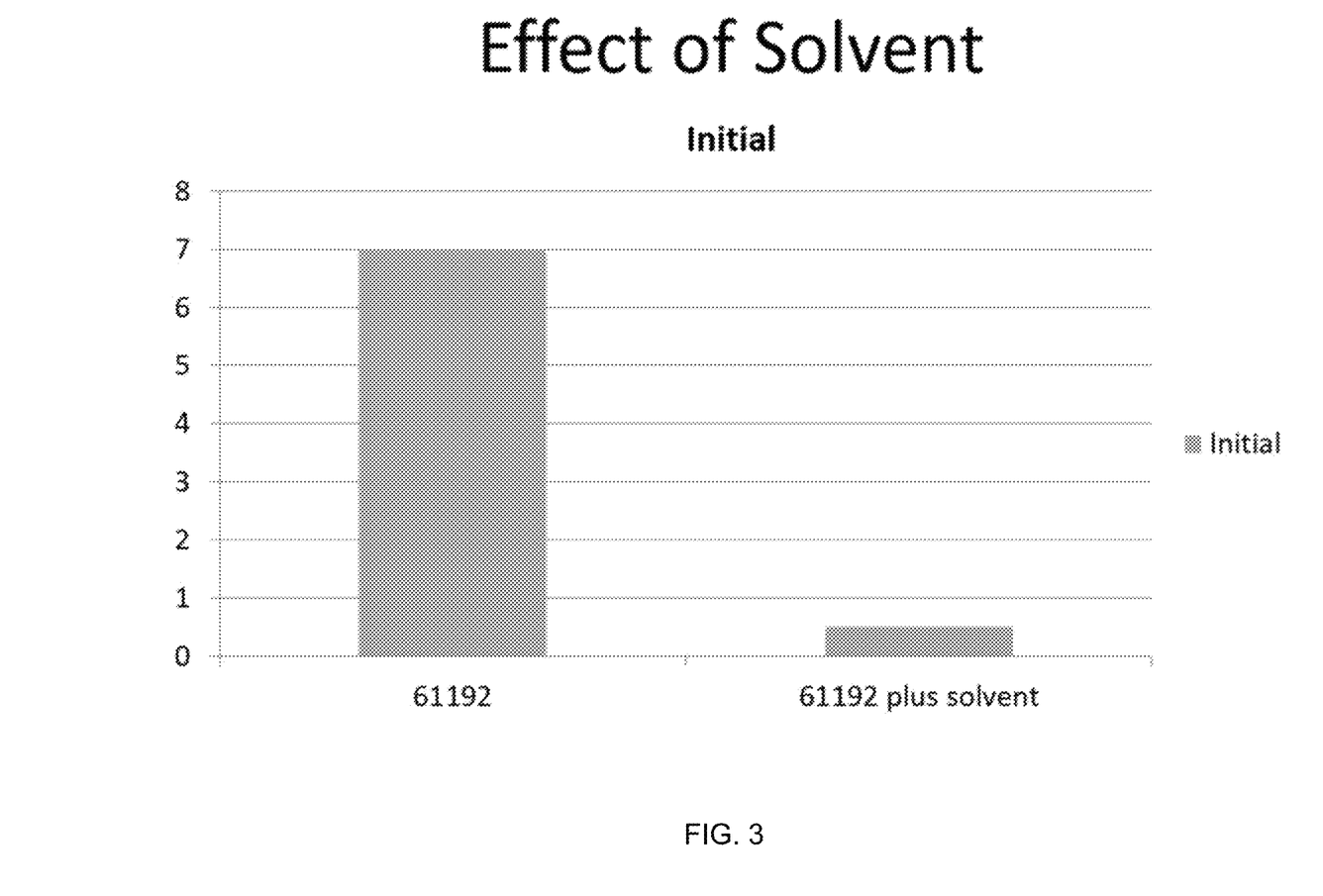
FIG. 3 is a graph related to the effect on initial performance of hairbrushes treated with treatment solutions containing a cross-linked acrylate polymer, ACRYGEN® 61192, that were prepared with and without a solvent (drying aid), respectively.
Figure 4:
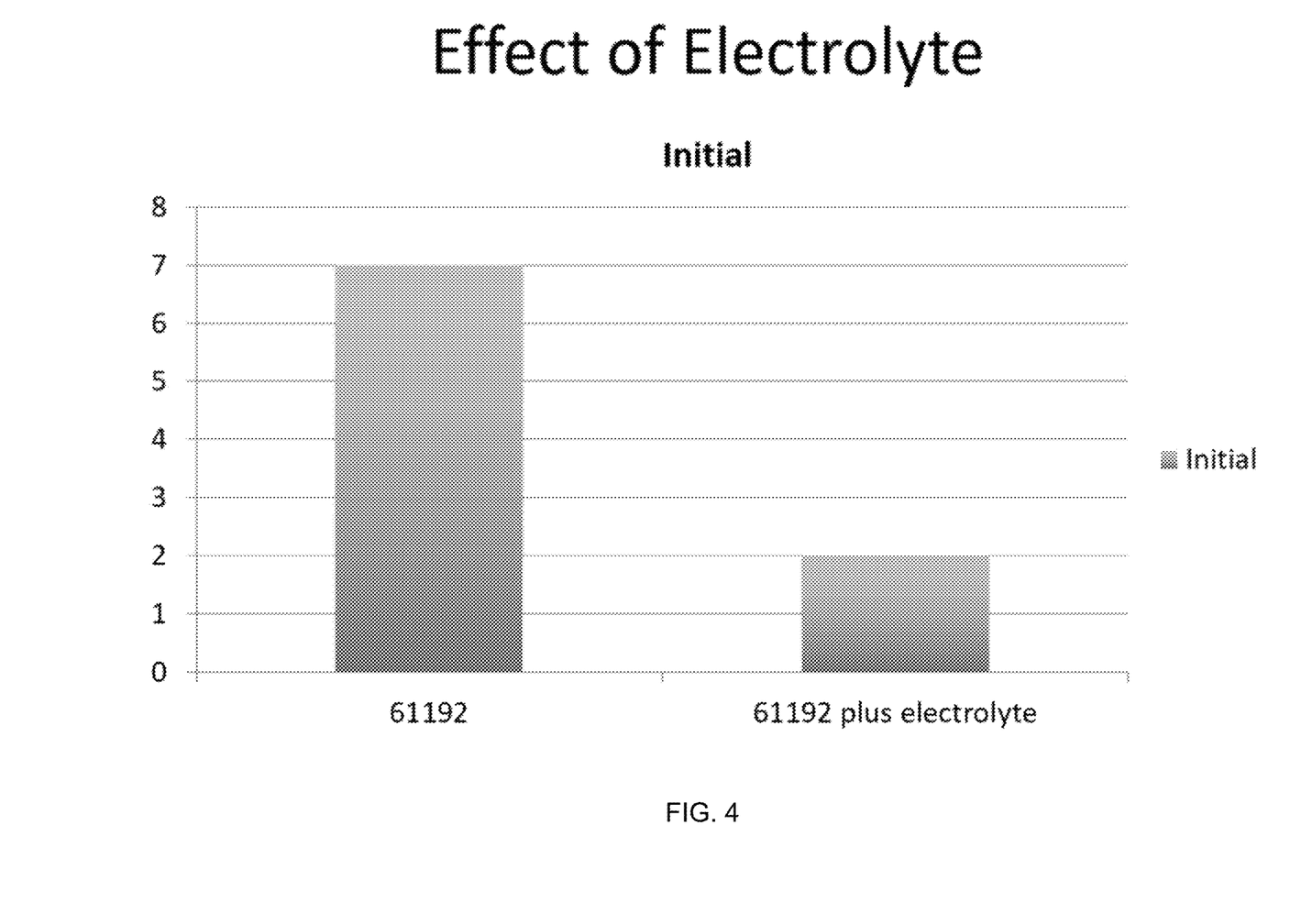
FIG. 4 is a graph related to the effect on initial performance of hairbrushes treated with treatment solutions containing cross-linked acrylate polymer, ACRYGEN® 61192, that were prepared with and without an electrolyte (catalyst), respectively.

Apply each test treatment solution A-D to a separate hairbrush. Brush the hair of a human subject using 250 brush strokes per hairbrush, recording the intensity of the tropical-scent fragrance at the following intervals: initially (after 5 brush strokes), after 50 brush strokes, after 100 brush strokes, and after 250 brush strokes. The intensity of the fragrance is assessed on a scale of 0 to 9, wherein 0 indicates no detectable fragrance, 5 indicates a noticeable level of fragrance, and 9 indicates a strong level of fragrance. The results of this testing are provided in FIG. 1. These results show that the treatment solutions containing acrylic binders (i.e., treatment solutions A and B) showed superior performance by continuing to release detectable levels of fragrance even after 250 brushes.

All references cited and/or discussed in this specification are incorporated herein by reference in their entireties and to the same extent as if each reference was individually incorporated by reference.

What is claimed is:

1. A treatment solution for adhering fragrance microcapsules to a hard surface, comprising:
   water; and
   microcapsules of polymer encapsulated fragrance, wherein the microcapsules comprise a hydrophobic composition comprising a fragrance material encapsulated within water-insoluble polymeric materials, wherein the water solubility of the fragrance material is 0.001 mol/L or less, and wherein the microcapsules are coated with a water-soluble binding agent coating that comprises a binding agent having a water solubility of at least 0.1 mol/L,
   wherein the binding agent coating covers at least 80% of an outer surface of the microcapsules such that the microcapsules adhere to the hard surface and remain friable;
   wherein the treatment solution contains water as the only solvent outside of the microcapsules, and
   wherein the microcapsules do not contain any surfactants or fixatives.

2. The treatment solution of claim 1, wherein a weight ratio of binding agent to microcapsule is in the range of about 1:1 to about 4:1.

3. The treatment solution of claim 1, wherein the binding agent comprises a cross-linked acrylate polymer.

4. The treatment solution of claim 1, comprising 10 vol % microcapsules and 10 vol % binding agent.

5. The treatment solution of claim 1, wherein the fragrance material is in the form of a liquid.

6. The treatment solution of claim 5, wherein the fragrance material comprises an aroma selected from food, vegetable, fruit, plant, floral, spice, and natural environment aromas, and combinations thereof, dispersed in a non-aqueous liquid.

7. The treatment solution of claim 1, wherein the fragrance material comprises isopropyl myristate, diethyl phthalate, or a combination thereof.

8. The treatment solution of claim 1, wherein the microcapsules comprise fragrance material in an amount of about 0.1% to about 50% by weight, based on the total weight of the microcapsules.

9. The treatment solution of claim 1, wherein the microcapsules have an average diameter of about 0.01 µm to about 300 µm.

10. The treatment solution of claim 1, wherein the microcapsules comprise an outer polymeric shell and an inner liquid core, wherein a weight ratio of shell to core is 1:10 to 1:500.

11. The treatment solution of claim 1, wherein the binding agent comprises reactive functional groups capable of chemically binding to a hard surface, wherein the reactive functional groups comprise one or more groups selected from acid anhydride groups, amino groups, N-substituted amino groups, epoxy groups, glycidyl groups, hydroxyl groups, isocyanate groups, urea groups, aldehyde groups, ester groups, ether groups, alkenyl groups, alkynyl groups, thiol groups, disulphide groups, silyl groups, silane groups, glyoxal-based groups, aziridine-based groups, 2,4-pentadione, malonic acid, acetylacetone, ethylacetone acetate, malonamide, acetoacetamide and its methyl analogues, ethyl acetoacetate, isopropyl acetoacetate, halo groups, hydrides, and combinations thereof.

12. The treatment solution of claim 1, wherein the binding agent does not comprise acrylic acid containing carboxylic groups.

13. The treatment solution of claim 1, wherein the microcapsules are controlled release microcapsules.

14. The treatment solution of claim 1, wherein the binding agent is dissolved in water as the only solvent in the binding agent coating.

15. The treatment solution of claim 1, wherein the polymeric materials are selected from gelatin, polyurethane, polyolefin, polyamide, polyester, polyolefin, protein, polysaccharide, modified cellulose, gums, polyacrylate, polystyrene, polyesters, lipids, silicone and siloxane resins, chitosan, epoxy resins, aminoplast polymers, and combinations thereof.

16. The treatment solution of claim 1, wherein the hard surface is selected from the group consisting of plastic, glass, ceramic, wood, fiberglass, metal, stone, coated surfaces, painted surfaces, and combinations thereof.

17. The treatment solution of claim 1, wherein the binding agent comprises an acrylic acid polymer or copolymer containing carboxylic acid groups.

* * * * *